United States Patent [19]

Sherwin et al.

[11] 4,087,623

[45] May 2, 1978

[54] CATALYST RECOVERY PROCESS

[75] Inventors: Martin Barry Sherwin, Wayne; Robert Hansen, West Caldwell, both of N.J.

[73] Assignee: Chem Systems, Inc., New York, N.Y.

[21] Appl. No.: 728,551

[22] Filed: Oct. 1, 1976

[51] Int. Cl.² ............................................. C07C 67/05
[52] U.S. Cl. .................................... 560/246; 423/504
[58] Field of Search ..................... 260/497 R; 560/246

[56] References Cited

U.S. PATENT DOCUMENTS

| | | | |
|---|---|---|---|
| 2,780,528 | 2/1957 | Fossan et al. | 260/635 R |
| 3,770,813 | 11/1973 | Kollar | 260/497 R |
| 3,884,965 | 5/1975 | Kollar | 260/497 R |

FOREIGN PATENT DOCUMENTS 1,148,210  12/1957  France.

*Primary Examiner*—James O. Thomas, Jr.
*Assistant Examiner*—Michael Shippen
*Attorney, Agent, or Firm*—Bert J. Lewen

[57] ABSTRACT

Disclosed is a method of removing iodine-containing compounds from the reaction product of iodine-catalyzed acetoxylation, wherein an olefin is reacted with oxygen and a carboxylic acid, and the iodine is recycled to the reactor.

6 Claims, No Drawings

CATALYST RECOVERY PROCESS

This invention is a method of removing catalyst-containing compounds from a reaction product and recycling the catalyst to the reactor. More specifically this invention is a method of removing iodine-containing compounds from vicinal glycol esters produced by the iodine-catalyzed acetoxylation of an olefin with oxygen and a carboxylic acid and recycling iodine in an active form to the reactor.

Recent technical literature indicates the usefulness of vicinal glycol esters as precursors for certain important chemicals. For example, U.S. Pat. No. 3,586,716 teaches the hydrolysis of esters such as ethylene glycol mono- and diacetate to ethylene glycol, and German Offenlegungsschrift No. 2,412,136 discloses a method of cracking propylene glycol monoacetate to propylene oxide.

These esters are produced by the acetoxylation of an olefin with oxygen and a carboxylic acid using a homogeneous liquid-phase catalyst system, usually one containing a halogen, most desirably iodine. When iodine is employed during the reaction, it reacts to form a variety of compounds the majority of which are organic. For reasons explained below, substantially all of the iodine must be removed from the esters before they are further utilized, and the iodine must be recycled to the reactor in an active form with as little loss as possible.

A large plant producing these esters requires 5,000 to 30,000 pounds of iodine to be fed to the reactor per hour. If the iodine recovery-recycle efficiency is 95%, that is, 5% of the iodine charged to the reactor is not recovered from the effluent and recycled, the iodine make-up is 2.0 to 12.0 million pounds per year. With a 99% recovery and recycle efficiency, the annual make-up of iodine is 0.4 to 2.4 million pounds/year. However, iodine is in short supply (the 1974 U.S. consumption was 9 million pounds, 80% imported) and is expensive (the 1975 price was over $1 per pound).

Furthermore, if iodine is not removed from the crude vicinal glycol esters, the iodine may contaminate the various end-products produced from these esters. For example, ethylene glycol produced from crude ethylene glycol acetates made with iodine catalyst but which are not treated in accordance with the method of this invention contains too much iodine to be used as synthetic fiber feed-stock. Thus for an iodine-catalyzed acetoxylation process to be technically and economically feasible, the esters must be highly purified, and the iodine catalyst recovery-recycle efficiency must be very high. In accordance with the invention, a method for treating the acetoxylation reactor effluent has now been developed which produces highly purified esters and concommitantly recovers and recycles the iodine catalyst at very high efficiency.

Briefly, the method consists of five steps. First, the acetoxylation reactor effluent is fractionated to produce several cuts, one of which is a crude ester cut containing some (approximately one-third to one-twentieth) of the iodine fed to the acetoxylation reactor. Additional fractionation cannot completely remove this remaining iodine (primarily organic iodine compounds) because of the closeness of the respective boiling points. The other cuts from fractionation, containing the rest of the iodine, are recycled to the reactor.

Second, the crude esters from fractionation are contacted in the liquid phase with certain basic materials to convert the contained iodine compounds to inorganic iodine salts. Third, the esters are separated from the salts and are ready for further processing (e.g., cracking and hydrolysis). Fourth, elemental iodine is liberated from these salts by a peroxidation reaction which also produces a base. Fifth, the elemental iodine is separated from the peroxidation reaction mixture and is recycled to the acetoxylation reactor. The base from step 4 may be recycled to the second step.

Most of the prior art concerning iodine removal or recovery concerns removal of inorganic iodine compounds from vapors and is not relevant to the present invention. The most pertinent U.S. prior art are U.S. Pat. Nos. 2,385,483; 3,394,078; 3,405,195; and 3,884,965.

In U.S. Pat. No. 2,385,483, relating to iodative dehydrogenation, a solution containing organic iodine compounds is hydrolyzed to form iodine salts, and the salts are separated and oxidized, thereby producing a crude stream containing elemental iodine. The stream is concentrated and mixed with sulfuric acid, and inert gas is used to strip the iodine from the solution, the iodine being recovered overhead. That method, patented in 1942, is unsatisfactory for treating an acetoxylation reactor effluent because (i) it does not provide for first removing iodine compounds separable by fractionation (about two-thirds to 95% the total), thus tripling the consumption of hydrolysis and oxidizing reagents; (ii) it consumes large quantities of inert gas and sulfuric acid; (iii) the stripping-recovery system is overly complicated and requires disposal of inert gas and sulfuric acid streams, both containing trace quantities of iodine and (iv) it does not regenerate any basic reagent.

In U.S. Pat. No. 3,394,078, organic iodides are removed from a stream from an iodative dehydrogenation process by contacting the stream with alkali metal and dimethylsulfoxide at ambient temperature. That method is not applicable here because (i) dimethylsulfoxide would contaminate the product esters; (ii) no pre-fractionation is used, thus greatly increasing consumption of reagents; (iii) the iodine is not recovered or recycled; and (iv) it does not regenerate any basic reagent.

In U.S. Pat. No. 3,405,195, organic iodides formed during iodative dehydrogenation are reacted in the liquid phase with alkali metal hydroxides or ammonium hydroxide at 1000 to 3000 psig and 250° to 375° C to produce water-soluble iodides. That method is unsuitable for treating the acetoxylation reactor effluent because (i) it lacks a pre-fractionation step; (ii) the operating conditions require high energy input and could cause product (vicinal esters) degradation; and (iii) the iodine is not recovered or recycled; (iv) it does not regenerate any basic reagent.

U.S. Pat. No. 3,884,965 claims a method of removing halogen compounds from an acetoxylation reactor product, but that method, which is analogous to steps 2 and 3 only of the instant invention, is unsuitable here because (i) there is a brief mention of but no teaching regarding pre-fractionation of the effluent; (ii) there is no teaching regarding recovery and recycling of the halogen in an active form, an economic necessity and an integral feature of the instant invention; (iii) waste disposal of a halogen-containing stream is required; (iv) the use of certain compounds which are totally ineffective in step 2 of this invention, e.g., calcium compounds, is advocated; and (v) there is no teaching regarding base recovery and recycle.

Thus there is no satisfactory method in the prior art which could accomplish the twin goals of (i) substantial purification of the esters, and (ii) recovery and recycle of iodine in an active form at very high efficiency.

Considering the foregoing, the results achieved by the instant invention are particularly surprising. Recognizing that the iodine compounds must be removed in order to attain proper ester purity and for recovery and recycle, the conventional approach would be to react the iodine materials with an inorganic base (e.g., a Group IA Compound) so as to form inorganic iodides which could be readily separated by fractionation. This approach was further suggested by the fact that the inorganic iodides were known to be an active form of catalytic material. Unfortunately, this procedure suffers from many drawbacks. In order to fully convert the iodine material, a large stoichiometric excess of the base is required. This procedure proves to be extremely cumbersome, and requires a substantial amount of base for treating the reactor effluent. Most importantly, recycle of the inorganic iodides (economically necessary) is impossible because it is difficult to free them of the excess base which must be employed but which cannot be fed to the acetoxylation reactor, and a build-up of metal will occur in the acetoxylation reactor.

In accordance with this invention, it has been discovered that the objects of purification of the ester and high recovery and recycle of the iodine and base can be achieved by first performing a prefractionation step in which the esters are separated from high- and low-boiling iodine compounds formed during the reaction (about two-thirds of all iodine compounds).

Only after the removal of the bulk of the iodine compounds by the fractionation step, is the ester treated with a Group IA metal compound. Since the amount of iodine remaining in the esters is only 5 to 30% of the iodine initially charged for reaction, the amount of the Group IA metal compound required is substantially reduced. The inorganic iodides formed may be readily separated from the ester and the iodine recovered from the inorganic iodides with a minimum amount of equipment and treating chemicals, and represents a substantial improvement over the process wherein the entire reactor effluent is treated.

Furthermore, and quite surprisingly, it has been found that the organic iodine compounds removed during the fractionation step contain catalytically active iodine and may therefore be recycled directly to the acetoxylation reactor. Accordingly, the conversion of organic iodine compounds recovered by fractionation to the conventional catalyst form is unnecessary, thus providing a further simplification in the overall process.

The olefins employed in acetoxylation are the $C_2$ to $C_6$ olefins, preferably ethylene and propylene. The carboxylic acids are the $C_2$ to $C_8$ carboxylic acids, preferably acetic and propionic acids, and most preferably acetic acid.

The first step of the invention is fractionating the acetoxylation reactor effluent so as to remove low- and high-boiling iodine compounds from the esters and recycling these iodine compounds to the reactor.

The fractionation may be accomplished by flash vaporization, stripping, evaporation, distillation, and the like. The esters generally should not be held at temperatures above approximately 300° C for more than several minutes to prevent degradation. The normal boiling points of these esters are in the range of 160° 1 to 200° C, thus fractionation need not necessarily be carried out under vacuum.

The effluent from the acetoxylation reactor contains the esters, unreacted carboxylic acid, iodine compounds, water of reaction, and dissolved gases. Preferably on commercial scale the fractionation is carried out in at least two stages so that a light overhead containing light iodine compounds, substantially free of the esters, and a heavy bottoms containing heavy iodine compounds, substantially free of the esters, may be obtained, as will be understood by one skilled in the art. "Iodine Lights," "Iodine Intermediates," and "Iodine Heavies," are hereinafter used to indicate compounds with vapor pressures higher than, equal to, and lower than those of the esters, respectively.

A preferred fractionating scheme is to flash the reactor effluent to recover dissolved oxygen and olefin for recycle to the reactor, and then feed the remaining liquid to an evaporator and evaporate overhead all compounds boiling lighter than the Iodine Heavies. The bottoms liquid, containing the Iodine Heavies, is recycled to the acetoxylation reactor.

The evaporator overhead is fed to a first column in which all compounds boiling lighter than the esters and Iodine Intermediates are distilled overhead. The feed to this column may optionally be partially condensed to reduce the vapor loading on the column. A reflux ratio (L/D) less than 3/1 and fewer than 50 real trays are generally needed in this first column, but, as will be understood by one skilled in the art, the choice is determined by an optimization of all parameters.

The unreacted carboxylic acid, water, and Iodine Lights are contained in the distillate from this first column. The carboxylic acid and Iodine Lights are dried by conventional and well-known techniques such as distillation, extractive distillation, azeotropic distillation, extraction, etc., in a second column. If acetic acid is the carboxylic acid employed in the acetoxylation reaction, azeotropic distillation with benzene is preferred. After partial or complete drying, the degree being determined by optimization, the carboxylic acid and Iodine Lights are recycled to the acetoxylation reactor. It is usually economic to allow a small amount of water to remain in this recycle stream (i.e. 1 to 5%). Drying with benzene has no effect on the reactivity of the Iodine Lights.

The result of this first step is to produce a crude ester stream contaminated with only Iodine Intermediates, and to recycle Iodine Lights and Iodine Heavies to the reactor, where they will provide the iodine for catalysis.

The second step of the invention is contacting the solution of esters and Iodine Intermediates in the liquid phase with a reactive metal compound to convert organic to inorganic iodine. The reactive metal compounds of this invention are the carbonate, hydroxide, and carboxylate of Group IA metals of the Periodic Table. Preferably a carboxylate of lithium, sodium, or potassium is used. Most preferably are the lithium, sodium, and potassium carboxylates where the carboxylate moiety corresponds to the carboxylic acid used in the acetoxylation reaction. For example, if reacting ethylene, acetic acid, and oxygen to form ethylene glycol acetates, lithium acetate, sodium acetate, and potassium acetate are the most preferred compounds for this step of the invention. This reaction is known art (*Organic Chemistry,* Fuson and Snyder, John Wiley & Sons, 1954, pp. 251, 265–69; *Organic Synthesis,* Migrdichian, Reinhold Publishing Corp., 1957, Vol. I, pp. 526–529, 535; *Principals of Organic Chemistry,* English and Cassidy, McGraw-Hill Book Co., 1956, pp. 171-177; and U.S. Pat. No. 3,884,965).

The amount of reactive metal compound employed is 1-10 equivalents of metal per equivalent of iodine remaining in the esters, and preferably 1.5 to 4.0 equivalents per equivalent of iodine. The reaction temperature is from 80° to 250° C and preferably from 140° to 200° C, and the pressure should be sufficient to maintain the mixture primarily in the liquid phase, but a boiling system could be employed. Required contact time varies with the temperature. Generally, contact times of from 1 minute to 5 hours may be employed; however, it is preferred that contact times be from 5 minutes (for temperatures around 200° C) to 30 minutes (for temperatures around 140° C).

To simplify addition and metering of the metal compound during the first step, the compound may be dissolved in a suitable solvent such as water or the carboxylic acid employed during acetoxylation. However, the solvent should preferably be removed from the reaction zone after sufficient reactive metal compound has been added. This may be accomplished using standard distillation techniques.

At the end of the contact period, most of the organic iodine has been converted and the crude esters contain salts, i.e., the excess metal compound and the metal iodide.

The third step of the invention is separation of the esters from these salts. Various standard techniques may be used, such as steam stripping, distillation with a chaser solvent, or evaporative crystallization. The particular method used is not critical to the practice of this invention, as will be understood by one skilled in the art. The iodine content of the recovered esters is generally in the ppm range; however, if iodine removal after these two steps (steps 2 and 3) is not sufficient, they may be repeated.

The fourth step of the invention is the reaction of the metal iodide with a carboxylic acid and hydrogen peroxide to yield elemental iodine, a metal carboxylate, and water. Although this reaction itself is known in the art (*Handbook of Analytical Chemistry*, 1st Edition, Meites, McGraw-Hill, 1963, p. 3-69, rx. 77 ), it has formerly been used generally only under different conditions in an analytical test for hydrogen peroxide, not to produce iodine.

It is preferred, though not essential, that the salts recovered in step 3 be substantially free from organics before processing in accordance with step 4. Organics may interfere with crystallization of the elemental iodine produced. Residual organics (e.g., the esters, a chaser solvent, if used in step 3, etc.) may be removed from the salts by standard drying techniques.

The reaction of step 4 is carried out in the liquid phase at temperatures from 10° to 80° C, and preferably at temperatures from 10° to 35° C. Operating pressure is not a critical parameter and moderate pressures above atmospheric are satisfactory. The quantity of acid employed is from 100 to 200% of theory, and the peroxide 80 to 120% of theory. Higher ratios may be used but are not economic. The preferred amounts of acid and peroxide are 100 to 120%, and 80 to 100% of theory, respectively. Neither water nor the other salts present interfere with the reaction, which is highly exothermic, producing about 50,000 BTU/lb-mole of metal iodide converted.

A most convenient and preferred mode of executing this peroxidation step is dissolving the salts recovered in step 3 in the required amount of acid and adding water sufficient to reduce the salts concentration to 10 to 50% and more desirably to 25 to 40%. The hydrogen peroxide is then added to the solution at a rate slow enough to prevent an undesirable exotherm. On commercial scale, means for rapidly removing the heat of reaction are required. Cooling coils in the peroxidation reaction vessel and a cooling jacket on the vessel can be used. Permitting the reaction mixture to boil will also remove heat. If a metal carboxylate is employed in step 2, desirably the corresponding carboxylic acid is used in step 4.

In the most preferred embodiment of the invention, the reactive metal compound of step 2 is the lithium, sodium, or potassium carboxylate of the carboxylic acid used in the acetoxylation reaction, the carboxylic acid of step 4 is that used in the acetoxylation reaction, and the lithium, sodium, or potassium carboxylate produced in step 4 is recycled (after step 5) for use in step 2, thereby achieving substantial economies by virtue of closed-loop operation with respect to the reactive metal compounds.

Thus if acetic acid is used in the acetoxylation reaction, an acetate such as potassium acetate is used in step 2, the salts recovered in step 3 are the excess potassium acetate and the potassium iodide formed, the preferred carboxylic acid in step 4 is acetic acid, and the potassium acetate formed in the step 4 reaction is recycled for use in step 2. In this case, the step 3 reaction would be

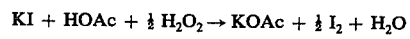

$$KI + HOAc + \tfrac{1}{2} H_2O_2 \rightarrow KOAc + \tfrac{1}{2} I_2 + H_2O$$

where OAc represents the acetoxy radical.

After the peroxide addition has been completed, substantially all the metal iodide has been converted to elemental iodine. The elemental iodine may exhibit itself as a crystalline precipitate if the mixture is free of organic compounds (glycol esters, carboxylic acid, and the like), or remain in solution if large quantities of organics are present. Most often, however, the iodine will be present in both forms.

The final step of the invention, step 5, is the recovery of the iodine from the peroxidation reactor effluent. The crystallized iodine is easily recovered by known techniques such as filtration, centrifugation, and then is recycled to the acetoxylation reactor. The dissolved iodine can also be recovered by known techniques, such as adsorption on activated carbon, crystallization, and sublimation. If a bed of activated carbon is used, the adsorbed iodine can be desorbed by flushing the bed with hot carboxylic acid, preferably the carboxylic acid used in the acetoxylation reactor, or by stripping with a stream of hot inert gas, with subsequent recovery from the gas by scrubbing with a carboxylic acid, preferably the acid used in the acetoxylation reactor. The iodine-carboxylic acid stream is then recycled to the acetoxylation reactor.

The following examples illustrate the practice of the invention.

EXAMPLE 1

1,060 g of acetic acid, 6.67 g of tellurium dioxide, and 50.5 g of elemental iodine are placed in a one-gallon agitated titanium autoclave which is then heated and pressurized with nitrogen to 180° C and 235 psig. A 90:10 (by volume) mixture of propylene and oxygen is then sparged into the reactor at the rate of 8 liters (STP)/min for 3 hours at the end of which the autoclave liquid (1441 g) contains 56% propylene glycol mono- and diacetates.

Pressure is reduced and the 1441 g are transferred to a rotary evaporator. Fifty grams of acetic acid are used to rinse the autoclave and then are added to the evaporator. A hot oil bath at 160° C supplies the required heat, and 1,283 g (containing 43.24 g iodine) are evaporated overhead at 100 mm Hg. The heel, 208 g (containing 7.26 g iodine, Iodine Heavies, and the tellurium) is recycled to the autoclave.

The evaporator overhead is condensed and placed in a three-liter three-neck flask equipped with thermometer and nitrogen sparge tube. A 10-plate Oldershaw column sits on top of and is connected to the flask. The column is equipped with a water-cooled condenser, a solenoid to control the reflux ratio, and a thermometer. The following cuts are obtained overhead:

| Cut | Overhead P(mm Hg) | Overhead T (° C) | Reflux Ratio (L/D) | Quantity (g) | Iodine Content (g) |
|---|---|---|---|---|---|
| 1 | 100 | 60–67 | 1/2 | 484 | 3.15 |
| 2 | 100 | 67–110 | 2/1 | 43.4 | 5.52 |
| 3 | 100 | 110–122 | 2/1 | 123.1 | 10.27 |
| 4 | 100 | 122–126 | 2/1 | 451.5 | 8.46 |
| 5 | 20 | 126–131 | 1/1 | 75.4 | 0.49 |

The heel, approximately 100 g, containing 15.35 g of the Iodine Heavies and esterification heavies is recycled to the autoclave.

Cut 1, containing primarily water and acetic acid, is dried azeotropically with benzene and recycled to the autoclave. Cut 2, containing primarily Iodine Lights and some esters, is recycled to the autoclave. Cut 3, containing esters and some Iodine Lights and Intermediates, is recycled to the autoclave.

Make-up acetic acid and iodine to establish the initial amounts are added to the autoclave and it is heated to 180° C and pressurized to 235 psig. A 90:10 (by volume) mixture of propylene and oxygen is again sparged into the reactor. Similar productivities of propylene glycol mono- and diacetates are obtained at the end of the reaction period, thereby indicating the ability to recycle the iodine compounds separated by fractionation (step 1) to the reactor with no loss in activity.

Cuts 4 and 5, primarily product esters, are combined, and 77.5 g of this material, containing 1.7% iodine (0.0104 equivalents), are placed in a 250 ml three-neck round bottom flask equipped with magnetic stirrer, thermometer, $N_2$ sparge tube, and condenser. The flask temperature is raised to 160° C, and 2.03 g of potassium acetate (0.0207 equivalents, 100% excess) are added, after which the mixture is stirred for approximately 15 minutes, then cooled, and filtered to remove the undissolved salts. Approximately 75 g of filtrate are recovered and placed in a 250 ml distillation flask. Distillate (product esters) collected at 125° C under 100 mm Hg contains less than 50 ppm iodine, indicating a 99+% removal of iodine. There is no product degradation. This illustrates steps 2 and 3 of the invention.

EXAMPLE 2

Twenty six and one-half g of recovered crude acetates, similar in composition to cuts 4 and 5 of Example 1 and containing 1.7% iodine, are heated to 160° C in a 100 ml three-neck round bottom flask equipped as in Example 1. While agitating the flask contents, 0.95 g of $Na(C_2H_3O_2).3H_2O$ (100% excess) are added, agitation is continued for 20 minutes, and the contents are cooled. A micro distillation apparatus is employed to separate the product esters from the salts. Vacuum distillation at 100 mm Hg gives an ester product containing less than 100 ppm iodine. This illustrates an alternative embodiment of steps 2 and 3 of the invention.

EXAMPLE 3

The acetoxylation reaction of Example 1 is repeated at similar conditions, but with ethylene instead of propylene and barium iodide instead of iodine. At the end of the reaction period, the autoclave contains ethylene glycol mono- and diacetates which are recovered by means of evaporation and distillation as in Example 1. The evaporator heel, distillation column heel, and the distillation cuts other than the recovered acetate cuts are recycled to the autoclave (after removing water of reaction).

One hundred g of recovered crude acetates, containing 1.67% (0.0133 equivalents) iodine, are placed in the 250 ml three-neck round-botton flask of Example 1. To the flask are added 5.22 g of 50% aqueous potassium acetate and the contents are agitated and heated to 160° C. Temperature is maintained for 15 minutes and then the mixture cooled. To facilitate distillation and heat transfer, 9.3 g of Witco 40 white mineral oil [72% paraffinic ($C_{14}$–$C_{20}$) and 28% naphthenic; trademark of Witco Chemical Company] are added to the flask. Vacuum distillation yields 91 g of product esters containing 37 ppm of iodine, indicating a 99+% iodine removal efficiency. There is no Witco 40 in the distillate.

Fifteen grams of water are added to the residual salt-Witco 40 mixture in the flask to dissolve the salts. The mixture is phase separated. All of the Witco 40 is in the organic phase, which contains no iodine. The aqueous phase contains all of the excess potassium acetate and the potassium iodide formed. Eight-tenths g (0.0133 equivalents or 100% theory) of acetic acid are added to this phase while agitating and then 0.64 ml of 30% aqueous $H_2O_2$ solution are slowly added. With the system's temperature at all times below 40° C.

Fifteen minutes after peroxide addition is completed, the temperature is raised to evaporate water and sublime iodine. Iodine crystals are observed in the condenser. Unsublimed elemental iodine in the flask totals 0.49 g and elemental iodine recovered from the overhead system amounts to 0.8 g. The in-hand iodine recovery efficiency is only 80%, because of condenser overhead trap losses and the small quantities being handled, but 99+% of the iodine is converted to elemental form. The recovered elemental iodine is recycled to the autoclave and sufficient make-up acetic acid is added to bring the total to the amount of acetic acid originally in the unit. Also, a small amount of iodine (0.38 g) is added to the autoclave to replace that lost through the traps. Acetoxylation pressure and temperature are re-established and the ethylene-oxygen mixture is again sparged through the reactor. At the end of the reaction period (3 hours), the production of acetates is almost identical to that initially produced. This illustrates in detail steps 2–5 of the invention.

COMPARATIVE EXAMPLE 1

Approximately 64 g of crude propylene glycol acetates produced and recovered in the manner of Example 1, containing 2.11% iodine (0.0107 equivalents), 7.1 g of water, and 1.66 g of $Ca(OH)_2$ are charged to a 600 cc stirred autoclave. Conditions are maintained at 180° C and 220 psig (under nitrogen) for 1 hour. The mixture is then cooled and vacuum distilled, yielding an ester product containing 1.82% iodine. This indicates no removal of iodine.

COMPARATIVE EXAMPLE 2

Approximately 23 g of the same ester used in Comparative Example 1 (containing 2.11% iodine) and 0.65 g of calcium acetate are mixed at 140° C in a round-bottom flask for 2 hours. Micro distillation at 100 mm Hg gives an ester product containing 2.2% iodine, thereby further indicating the ineffectiveness of calcium compounds in step 2 of the invention.

We claim:

1. In a process for producing vicinal glycol esters by the acetoxylation reaction of an olefin, a carboxylic acid, and oxygen in the presence of an iodine catalyst, the improvement of recycling the iodine catalyst to the reactor comprising the steps in order:
   (a) fractionating the acetoxylation reactor effluent to separate at least some of the iodine compounds from the vicinal glycol esters and recycling at least some of the separated iodine compounds to the acetoxylation reactor;
   (b) contacting the vicinal glycol esters with a reactive metal compound in the liquid phase at temperatures from 80° to 250° C, wherein the reactive metal compound is the carboxylate of a Group IA metal of the Periodic Table, said carboxylate corresponding to the carboxylic acid used in the acetoxylation reaction, and wherein the amount of reactive metal compound is from 1 to 10 equivalents of metal per equivalent of iodine remaining in the esters after step (a), thereby forming a metal iodide;
   (c) separating the metal iodide;
   (d) contacting the metal iodide in the liquid phase with a carboxylic acid and hydrogen peroxide at temperatures from 10° to 80° C, wherein the molar ratio of carboxylic acid to metal iodide is at least 1/1 and the molar ratio of hydrogen peroxide to metal iodide at least 0.8/1, thereby forming elemental iodine and a metal carboxylate, wherein the carboxylate is the same as the carboxylate in step (b);
   (e) recovering the elemental iodine and recycling at least some of it to the acetoxylation reactor; and
   (f) recycling at least a part of the metal carboxylate formed in step (d) to step (b) to serve as the reactive metal compound.

2. The process of claim 1 wherein the amount of reactive metal compound of step (b) is from 1.5 to 4 equivalents of metal per equivalent of iodine.

3. The process of claim 1 wherein the temperature in step (b) is from 140° to 200° C.

4. The process of claim 1 wherein in step (d) the molar ratio of carboxylic acid to metal iodide is from 1/1 to 2/1 and the molar ratio of hydrogen peroxide to metal iodide is from 0.8/1 to 1.2/1.

5. The process of claim 1 wherein the reactive metal compound of step (b) is the carboxylate of lithium, sodium, or potassium.

6. The process of claim 1 wherein the olefin is ethylene or propylene, and the carboxylic acid is acetic acid.

* * * * *